United States Patent [19]

Kimura et al.

[11] Patent Number: 5,164,459
[45] Date of Patent: Nov. 17, 1992

[54] METHOD FOR TREATING THE SURFACE OF AN ABSORBENT RESIN

[75] Inventors: Kazumasa Kimura, Ikoma; Takumi Hatsuda; Kinya Nagasuna, both of Himeji, all of Japan

[73] Assignee: Nippon Shokubai Kagaku Kogyo Co., Ltd., Osaka, Japan

[21] Appl. No.: 502,735

[22] Filed: Apr. 2, 1990

[51] Int. Cl.$^5$ .................................................. C08F 8/14
[52] U.S. Cl. ................................. 525/384; 525/329.5; 525/329.6; 525/330.1
[58] Field of Search ........................................ 525/384

[56] References Cited

U.S. PATENT DOCUMENTS

| | | |
|---|---|---|
| 3,661,815 | 5/1972 | Smith . |
| 4,076,663 | 2/1978 | Masuda . |
| 4,497,930 | 2/1985 | Yamasaki . |
| 4,587,308 | 5/1986 | Makita . |
| 4,666,983 | 5/1987 | Tsubakimoto . |
| 4,734,478 | 3/1988 | Tsubakimoto . |

FOREIGN PATENT DOCUMENTS

| | | |
|---|---|---|
| 0224923 | 6/1987 | European Pat. Off. . |
| 0317106 | 5/1989 | European Pat. Off. . |
| 0318989 | 6/1989 | European Pat. Off. . |
| 2559158 | 8/1985 | France . |
| 2162525 | 2/1986 | United Kingdom . |

*Primary Examiner*—Bernard Lipman
*Attorney, Agent, or Firm*—Burns, Doane, Swecker & Mathis

[57] ABSTRACT

A method for treating the surface of an absorbent resin which comprises mixing (I) 100 parts by weight of an absorbent resin powder having a carboxyl group, (II) 0.01 to 30 parts by weight of a polyhydric alcohol, (III) 0 to 50 parts by weight of water and (IV) 0 to 60 parts by weight of a hydrophilic organic solvent, and heat-treating at a temperature in the range of 90° to 250° C. to treat the surface of said absorbent resin powder (I) until the reaction of said absorbent resin powder (I) with said polyhydric alcohol (II) is completed, wherein the time for completion of the reaction is the time that satisfies the following equation (a-1):

$$30 \leq (100 + C)B/A \leq 80 \qquad \text{(a-1)}$$

wherein A is absorption capacity of said absorbent resin powder (I) for physiological saline solution, B is the absorption capacity of the resultant treated absorbent resin for physiological saline solution, and C is parts by weight of said polyhydric alcohol (II) used per 100 parts by weight of said absorbent resin powder (I).

19 Claims, 1 Drawing Sheet

METHOD FOR TREATING THE SURFACE OF AN ABSORBENT RESIN

FIELD OF THE INVENTION

The present invention relates to a method for treating the surface of an absorbent resin. More particularly, it relates to a method for treating the surface of the absorbent resin by crosslinking the surface region of the absorbent resin using a crosslinking agent to obtain an absorbent excellent in absorption rate under pressure, water-retaining property under pressure and liquid permeability under pressure.

DESCRIPTION OF THE PRIOR ART

Attempts have been made heretofore to use an absorbent resin as one of the component materials for such sanitary articles as sanitary napkins and disposable diapers which function to absorb body fluids. Absorbent resins of this nature heretofore known to the art include a hydrolyzed starch-acrylonitrile graft polymer (Japanese Patent Publication SHO 49(1974)-43,395), a neutralized starch-acrylic acid graft polymer (Japanese Patent Laid-Open SHO 51(1976)-125,468), a saponified vinyl acetate-acrylic ester copolymer (Japanese Patent Laid-Open SHO 52(1977)-14,689), a hydrolyzed acrylonitrile copolymer or acrylamide copolymer (Japanese Patent Publication SHO 53(1978)-15,959), crosslinked products thereof, a partially neutralized polyacrylic acid, and a partially neutralized cross-linked polyacrylic acid (Japanese Patent Laid-Open SHO 57(1982)-34,101).

Characteristic properties expected in absorbent resins include high absorption capacity, high absorption rate, liquid permeability, and large gel strength. These characteristic properties, however, do not always show a positive correlation.

For example, an absorbent resin having a high absorption capacity generally possesses a low gel strength, forms what resembles "wetted clusters of flour" on contact with an aqueous liquid, suffers from impairment of liquid permeability, prevents the aqueous liquid to be dispersed throughout the entire volume of the particles of the absorbent resin, and has extremely low absorption rate. As a means of remedying these drawbacks, a method which comprises coating the surface of the particles of the absorbent resin with a surfactant or an involatile hydrocarbon has been introduced to the art. Though this method is indeed capable of improving the initial dispersibility of the aqueous liquid in the particles of the absorbent resin, it produces virtually no discernible effect in the improvement of the absorption rate of the individual particles.

Further, a method which comprises causing a specific cross-linking agent to react on the surface of the absorbent resin thereby heightening the cross-link density in the surface region of the absorbent resin has been known to the art (Japanese Patent Laid-Open SHO 58(1983)-180,233 and Japanese Patent Laid-Open SHO 61(1986)-16,903). When this method is used, the absorbent resin does not easily form wetted clusters on contact with an aqueous liquid and the aqueous liquid is easily dispersed throughout the entire particles of the absorbent resin. Thus, this method serves the purpose of improving the absorption rate of the absorbent resin to some extent. In recent years, the growing trend of absorbent articles particularly for sanitary applications toward better performance and better quality have been urging the absorbents used in such absorbent articles to offer higher quality of absorption rate. However, an actual absorbent article for sanitary use should absorb body fluids under pressure, so it has been clarified that the absorption property under pressure is important. For absorbent resins used as constituent materials for a sanitary material which absorbs body fluid, not only absorption rate, liquid permeability, and absorption capacity under no pressure, but also absorption rate, liquid permeability and absorption capacity under pressure are important, and high absorption rate under pressure, high liquid permeability under pressure, and high water-retaining property under pressure have been required. None of the prior art satisfies such requirements.

An object of the present invention is, accordingly, to provide a method for treating the surface of an absorbent resin.

Another object of the present invention is to provide an effective method for treating the surface of absorbent resin for obtaining an absorbent having high absorption rate under pressure, high liquid permeability under pressure, and high water-retaining property under pressure.

Still another object of the present invention is to provide an effective method for treating the surface of absorbent resin for obtaining an absorbent which can be dispersed between pulp fibers, has high absorption capacity even if it is contacted with an aqueous liquid under pressure, and has high liquid permeability without closing capillaries between the pulp fibers.

SUMMARY OF THE INVENTION

These objects are accomplished by a method for treating the surface of an absorbent resin which comprises mixing (i) 100 parts by weight of an absorbent resin powder having a carboxyl group, (II) 0.01 to 30 parts by weight of a polyhydric alcohol, (III) 0 to 50 parts by weight of water and (IV) 0 to 60 parts by weight of a hydrophilic organic solvent, and heat-treating at a temperature in the range of 90° to 250° C. to treat the surface of said absorbent resin powder (I) until the reaction of said absorbent resin powder (I) with said polyhydric alcohol (II) is completed, wherein the time for completion of the reaction is the time that satisfies the following equation (a-1):

$$30 \leq (100+C) B/A \leq 80 \tag{a-1}$$

wherein A is absorption capacity of said absorbent resin powder (I) for physiological saline solution, B is the absorption capacity of the resultant treated absorbent resin for physiological saline solution, and C is parts by weight of said polyhydric alcohol (II) used per 100 parts by wegiht of said absorbent resin powder (I).

According to the present invention, an absorbent having high absorption rate under pressure, liquid permeability under pressure, and water-retaining property under pressure is obtained by reacting the surface region of an absorbent resin powder (I) having a carboxyl group with a polyhydric alcohol (II) and completing the reaction of the surface treatment when the above-mentioned formula (a-1) is satisfied.

Further, the absorbent thus obtained shows high absorption rate and absorption capacity even if it is contacted with an aqueous solution under pressure when dispersed between pulp fibers, and has high liquid permeability without closing capillaries between pulp fibers, so if for example, it is used in a disposable diaper, a diaper having less leakage can be obtained.

EXPLANATION OF THE PREFERRED EMBODIMENT

Figure 1:
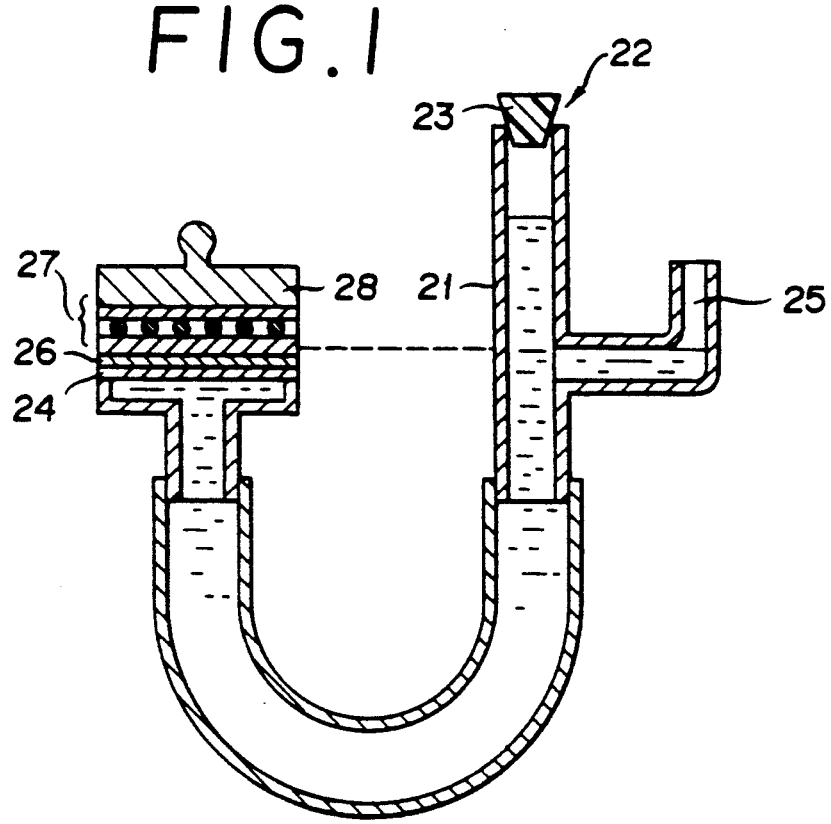
FIG. 1 is a sectional view of an apparatus for measuring water-retaining property under pressure.

For use in this invention, it is preferable that the absorbent resin powder (I) possesses a carboxyl group. The heretofore known carboxyl group-containing absorbent resins include a hydrolyzed starch-acrylonitrile graft polymer, a neutralized starch-acrylic acid graft polymer, saponified vinyl acetate-acrylic ester copolymers, hydrolyzed acrylonitrile or acrylamide copolymers, cross-linked products of such copolymers, a partially neutralized polyacrylic acid, and a partially neutralized cross-linked polyacrylic acid, invariably available in the form of powder, for example. These absorbent resin powders may be used either singly or in varying combinations of two or more members. The absorbent resin powder (I) is preferable, but not always required, to possess a cross-linked structure.

Though the amount of the carboxyl group to be possessed by the absorbent resin powder (I) is not specifically limited, it is preferable to be not less than 0.01 equivalent weight based on 100 g of the absorbent resin powder (I). In the case of the partially neutralized polyacrylic acid, for example, the proportion of the unneutralized portion thereof is preferable to be in the range of 1 to 50 mol %, preferably 5 to 40 mol %.

The form in which the absorbent resin powder (I) is used in the present invention is not specifically limited. It may be in the form of spheres obtained by reverse-phase suspension polymerization, in the form of flakes obtained by drum drying, or in the form of irregular particles obtained by crushing resin lumps, for example. Preferably, the absorbent resin powder is in the form of flakes or irregular particles.

The polyhydric alcohol (II) to be used in this invention has at least two hydroxyl groups per molecular unit. It is preferable to use, among polyhydric alcohols answering the description, one member or a varying combination of two or more members selected from the group consisting of ethylene glycol, diethylene glycol, triethylene glycol, polyethylene glycol, glycerol, polglycerol, propylene glycol, diethanolamine, triethanolamine, polyoxypropylene, oxyethylene-oxypropyle block copolymer, sorbitan fatty acid esters, polyoxyethylene sorbitan fatty acid esters, trimethylolpropane, pentaerythritol, 1,3-propanediol, and sorbitol.

The amount of the polyhydric alcohol (II) to be used in the present invention is to be in the range of 0.01 to 30 parts by weight, preferably 0.1 to 10 parts by weight based on 100 parts by weight of the absorbent resin powder (I). If this amount is less than 0.01 part by weight, even if it is heated for a long time, an increase of absorption rate under pressure, liquid permeability under pressure, and water-retaining property under pressure, cannot be recognized. Conversely, if the amount exceeds 30 parts by weight, it is difficult to obtain an effect corresponding to the increase of the amount, and the unreacted polyhydric alcohol (II) remains, so that it becomes not only a reason of various troubles, but also uneconomical.

For the purpose of ensuring the homogeneous mixing of the polyhydric alcohol (II) and the absorbent resin powder (I), the present invention uses water (III) 0 to 50 parts by weight and a hydrophilic organic solvent (IV) 0 to 60 parts by weight based on 100 parts by weight of the absorbent resin powder (I).

The water (III) is effective in promoting the permeation of the polyhydric alcohol (II) into the surface region of the absorbent resin powder (I). The water (III) is preferable to be used in an amount in the range of 0 to 50 parts by weight, preferably 0.1 to 50 parts by weight, more preferably 0.1 to 20 parts by weight, based on 100 parts by weight of the absorbent resin powder (I). If the amount is less than 0.1 part by weight, the effect of the addition is difficult to be recognized, and if the amount exceeds 50 parts by weight, the mixing of the water with the absorbent resin powder may possibly necessitate a powerful mixing device.

The hydrophilic organic solvent (IV) is only required to be capable of being uniformly mixed with the polyhydric alcohol (II) and refraining from producing any adverse effect on the performance of the absorbent resin powder (I). The hydrophilic organic solvents which fulfill this requirement include lower alcohols such as methanol, ethanol, n-propanol, isopropanol, n-butanol, isobutanol, sec-butanol, and t-butanol; ketones such as acetone, methylethyl ketone, and methylisobutyl ketone; ethers such as dioxane, tetrahydrofuran, and diethyl ether; amides such as N,N-dimethyl formamide and N,N-diethyl formamide; and sulfoxides such as dimethyl sulfoxide, for example.

The hydrophilic organic solvent (IV) is effective in uniformly dispersing the polyhydric alcohol (II) on the surface of the absorbent resin powder (I). The amount of this solvent desirable for the manifestation of this effect is in the range of 0 to 60 parts by weight, preferably 0.1 to 60 parts by weight based on 100 parts by weight of the absorbent resin powder (I). If this amount exceeds 60 parts by weight, the heat treatment consumes an unduly long time.

In the present invention, the mixture of the absorbent resin powder possessing a carboxyl group (I) with the polyhydric alcohol (II), is generally accomplished by spraying or dropping the polyhydric alcohol (II) or the mixture of the polyhydric alcohol (II) with water (III) and/or the hydrophilic organic solvent (IV) onto the absorbent resin powder (I) and mixing them.

The preferred mixing devices to be used for this mixing need to produce a large mixing force to ensure uniform mixing. Mixing machines and kneading machines may be effectively used. The mixing devices which are usable herein include cylindrical mixers, double-walled cone mixers, V-shaped mixers, ribbon type mixers, screw type mixers, fluidizing type mixers, rotary disc type mixers, gas-current type mixers, twin-arm type kneaders, internal mixers, muller type kneaders, roll mixers, and screw type extruders, for example.

The method of treating the surface of an absorbent resin in accordance with the present invention can be attained by mixing the absorbent resin powder (I) and the polyhydric alcohol (II) or by mixing the absorbent resin powder (I), the polyhydric alcohol (II), water (III), and the hydrophilic organic solvent (IV) and heating them. Heat treatment can be carried out during mixing the components (I) through (IV) or after mixing. Heat treatment can be carried out using a conventional drier or oven. For example, there are groove type mixing driers, rotary driers, disc driers, kneading driers, fluidized-bed type driers, gas flow type driers, and infrared ray driers. When the mixing of the components (I) through (IV) and heat treatment are carried out at the same time, a heat mixing type drier is used.

The temperature of the heat treatment is in the range of 90° to 250° C., preferably 120° to 200° C. If the temperature is lower than 90° C., the heat treatment proves to be uneconomical because it consumes an unduly long time. Conversely, if this temperature exceeds 250° C., the heat treatment demands careful attention because some, if not all, of the absorbent resins are liable to undergo thermal deterioration. So long as the temperature of the heat treatment is confined in this range of 90° to 250° C., the cross-linking reaction, providing for the full manifestation of the effect of this invention, can be accomplished in a short span of time without entailing the possibility of deteriorating or coloring the absorbent resin.

The invention resides in the method herein (I) 100 parts by weight of an absorbent resin powder possessing a carboxyl group is mixed with (II) 0.01 to 30 parts by weight of a polyhydric alcohol, (III) 0 to 50 parts by weight of water and (IV) 0 to 60 parts by weight of a hydrophilic organic solvent, and the reaction of the absorbent resin powder (I) with the polyhydric alcohol (II) is completed at a temperature of 90° to 250° C. to treat the surface of the absorbent resin powder, the time for completion of the reaction of the surface treatment being the time that satisfies the above equation (1-1), preferably the following equation (a-2):

$$40 \leq (100 + C) B/A \leq 70 \qquad (a-2)$$

If the (100+C) B/A in the equation (a-1) is (100+C) B/A > 80, only the cross-linking density at the region of the surface of the absorbent resin powder (I) increases, and although the increase of absorption rate corresponding to the increase of the cross-linking density is recognized, the increase of absorption rate under pressure and liquid permeability under pressure cannot be recognized. Further, the absorbent having high water-retaining property under pressure cannot be obtained. On the contrary, if the (100 +C) B/A in the equation (a-1) is 30 > (100+C) B/A, increase of the absorption rate under pressure and liquid permeability under pressure corresponding to the promotion of the reaction cannot be recognized, and it is not preferable, because the absorption capacity of the absorption thus obtained decreases remarkably compared to that of the starting absorbent resin powder (I) and original properties of the absorbent resin is damaged.

According to the preferred embodiment of the present invention, the object of the present invention can be accomplished by a method for the surface treating of an absorbent resin which comprises mixing (I) 100 parts by weight of an absorbent resin powder, (II) 0.01 to 30 parts by weight of a polyhydric alcohol, (III) 0 to 50 parts by weight of water and (IV) 0 to 60 parts by weight of a hydrophilic organic solvent in the presence of (V) a water insoluble fine powder wherein the time for completion of the reaction is the time that satisfies the following equation (b-1), $$30 \leq (100 + C + D) B/A \leq 80 \qquad (b-1)$$

preferably the following equation (b-2):

$$40 \leq (100 + C + D) B/A \leq 70 \qquad (b-2)$$

wherein A is the absorption capacity of said absorbent resin powder (I) for a physiological saline solution, B is the absorption capacity of the resultant treated absorbent resin for physiological saline solution, and C is parts by weight of said polyhydric alcohol (II) used per 100 parts by weight of said absorbent resin powder (I), and D is parts by weight of said water-insoluble fine powder (V) used per 100 parts by weight of the absorbent resin powder (I).

The water-insoluble fine powders (V) which are usable in the preferred embodiment of this invention include inorganic powders of silicon dioxide, titanium dioxide, aluminum oxide, magnesium oxide, zinc oxide, calcium phosphate, barium phosphate, diatomaceous earth, talc, zeolite, bentonite, kaolin, hydrotalcite, activated carbon, activated clay, and clayish minerals and organic powders such as cellulose powder, pulp powder, rayon, polyesters, polyethylene, polypropylene, polyvinyl chloride, polystyrene, nylons, and fine acryl resin, for example. Among other water-insoluble fine powders mentioned above, water-insoluble inorganic powders prove to be particularly desirable. The water-insoluble fine inorganic powders which are advantageously usable herein include silicon dioxide, titanium dioxide, aluminum oxide, magnesium oxide, zeolite, bentonite, kaolin, and hydrotalcite, for example.

The amount of the water-insoluble fine powder (V) to be used in the preferred embodiment is in the range of 0.01 to 10 parts by weight, preferably 0.01 to 5 parts by weight, based on 100 parts by weight of the absorbent resin powder (I).

The particle size of the water-insoluble fine powder (V) is preferably to be not more than 1,000 μm, more preferably not more than 50 μm.

In the preferred embodiment of this invention, the timing of the addition of the water-insoluble fine powder (V) to the reaction mixture may be fixed to suit any of the following procedures.

(i) The absorbent resin powder (I) is mixed with the water-insoluble fine powder (V) before it is mixed with the polyhydric alcohol (II), water (III) and the hydrophilic organic solvent (IV).

(ii) The absorbent resin powder (I) is mixed with the water-insoluble fine powder (V) at the same time that it is mixed with the polyhydric alcohol (II), water (III) and the hydrophilic organic solvent (IV).

(iii) The water-insoluble fine powder (V) is mixed with the product of the mixture of the absorbent resin powder (I) with the polyhydric alcohol (II), water (III) and the hydrophilic organic solvent (IV).

The timing of the procedure (i) in which the water-insoluble fine powder (V) is added in advance to the absorbent resin powder (I) or of the procedure (ii) in which the water-insoluble fine powder (V) is added at the same time that the absorbent resin powder (I) is mixed with the polyhydric alcohol (II), water (III) and the hydrophilic organic solvent (IV) is preferable.

As described above, by the method of mixing 100 parts by weight of the absorbent resin powder (I), 0.01 to 30 parts by weight of a polyhydric alcohol (II), 0 to 50 parts by weight of water (III), and 0 to 60 parts by weight of a hydrophilic organic solvent (IV), and heat-treating the surface region of said absorbent resin powder (I) at a temperature of 90° C. to 250° C., wherein the time for completion of the reaction is the time that satisfies the above-mentioned equation (a-1), and further by the method of mixing 100 parts by weight of an absorbent resin (I) 0.01 to 30 parts by weight of a polyhydric alcohol (II), 0 to 50 parts by weight of water and (IV) 0 to 60 parts by weight of a hydrophilic organic solvent, and heat-treating the surface region of said absorbent resin powder (I) at a temperature of 90° C. to 250° C. in the presence of a water-insoluble fine powder (V), wherein the time for completion of the reaction is the time that satisfies the above-mentioned equation (b-1), this invention produces an absorbent which has not only a high absorption rate, but also a high absorption rate under pressure and high liquid permeability under pressure as well as a high water-retaining property under pressure.

Further, the absorbent obtained by the present invention having the above-mentioned features, are useful as one of the component materials of such sanitary articles as sanitary napkins and disposable diapers and as a coagulant for sludge, as a dew-drop proofing agent for building materials, as a water-retaining agent for agriculture and horticulture, and as dryer.

Now, the present invention will be described more specifically below with reference to working examples. It should be noted, however, that the scope of this invention is not limited to these examples.

EXAMPLE 1

A jacketed twin arm type kneader of stainless steel measuring 10 liters in inner volume, 220 mm × 240 mm in the opening, and 240 mm in depth and provided with two Sigma type blades possessing a rotational diameter of 120 mm was stoppered with a lid. Into this kneader, a monomer component containing 5,500 g of an aqueous, solution of sodium acrylate possessing a neutralization ratio of 75 mol % and 1.7 g of trimethylol propane triacylate (0.025 mol % based on sodium acrylate possessing a neutralization ratio of 75 mol %) (the monomer concentration 37% by weight in the aqueous solution) was introduced and nitrogen gas was blown to displace the air entrapped inside the reaction system. Then, the two Sigma type blades were set rotating at rates of 46 rpm and, at the same time, the jacket was heated by passage of hot water at 35° C. As a polymerization initiator, 2.8 g of sodium persulfate and 0.14 g of L-ascorbic acid were added. Polymerization started four minutes after the addition of the polymerization initiator. The peak temperature inside the reaction system reached 82° C. after the elapse of 15 minutes following the addition of the polymerization initiator. The hydrated gel polymer had been divided into minute particles about 5 mm in size. The stirring was further continued. The lid was removed from the kneader 60 minutes after the start of the polymerization and the gel was removed from the kneader.

The minute particles of hydrated gel polymer thus obtained were spread on a 50-mesh metal gauze and dried with hot air at 150° C. for 90 minutes. The dried minute particles were pulverized with a hammer type crusher and sifted with a 20-mesh metal gauze to obtain a 20-mesh pass portion [absorbent resin powder (A-1)].

A liquid mixture containing 0.75 parts of glycerol, 3 parts of water and 12 parts of isopropanol was mixed with 100 parts of the absorbent resin powder (A-1).

The resultant mixture was charged into a bowl dipped in an oil bath (195° C.) and was subjected to heat-treatment for 45 minutes under stirring to obtain an absorbent (1).

The absorbent resin powder (A-1) and the absorbent (1) obtained as described above were tested for (i) absorption capacity, (ii) water-retaining property under pressure 10 min and 30 min, (iii) Liquid Permeability under pressure as follows;

(i) Absorption capacity: A pouch (40 mm × 150 mm) made of non-woven fabric after the fashion of a tea bag and filled evenly with about 0.2 g of a sample of absorbent resin powder (A-1) or absorbent (1) was immersed in an aqueous 0.9% NaCl solution for 60 min removed from the solution, left draining for 5 sec, removing water on 24 folded toilet paper having 60 cm for 10 seconds, and weighed.

$$\text{Absorption capacity (g/g)} = \frac{\text{Weight after absorption (g)} - \text{Blank(g)}}{\text{Weight of absorbent resin (g)}}$$

(ii) Water-retaining property under pressure: The test for the water-retaining property under pressure was carried out by the use of an apparatus configured as shown in FIG. 1. The upper end 22 of a buret 21 was stoppered with a plug 23 and a measuring stand 24 was set flush with an air inlet 25. On a glass filter (No. 1) 26 70 mm in diameter placed in the measuring stand 24, a filter paper, 0.20 g of a sample of absorbent resin powder (A-1) or absorbent (1), and a filter paper 27 were superposed and a weight of 0.2 psi was mounted thereon. The sample as sandwiched between the filter papers was left to absorbing synthetic urine (containing 1.9% of urea, 0.8% of Nacl, 0.1% of $CaCl_2$, and 0.1% of $MgSO_4$) for 10 to 30 minutes. At the end of the absorption, the volume (A ml) of the synthetic urine absorbed was measured.

$$\text{Water-retaining property under pressure (ml/g)} = A \text{ (ml)}/0.20 \text{ (g)}$$

Figure 2:
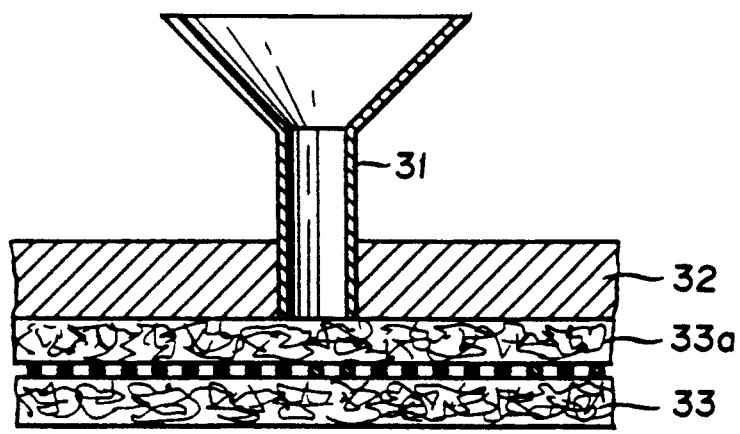
FIG. 2 is a sectional view of an apparatus for measuring liquid permeability under pressure.

(iii) Liquid permeability under pressure: The test for liquid permeability was carried out by the use of an apparatus configured as shown in FIG. 2. A model diaper was prepared by uniformly scattering 4.0 g of a sample of absorbent resin powder (A-1) or absorbent (1) 34 on a bed of 12 g of pulp 33 140 mm × 250 mm in area, superposing 12 g of pulp 33a on the scattered sample, and pressing the superposed layers under a load of 2 kg/cm². A weight 32 of 0.2 psi measuring 150 mm × 250 mm in area and provided at the center thereof with a synthetic urine inlet (31) was mounted on the model diaper. Then 100 ml of the synthetic urine was poured into the model diaper. After standing for 30 minutes, further when 150 ml of synthetic urine is added, the time which elapsed before the synthetic urine disappeared from the inlet was clocked.

(iv) Calculated value of formula: Water content (105° C.-3 hours) of the absorbent resin powder (A-1) was 2% (wet basis), the formula (a-1) substituted by P/0.98 = P' to calculate the value of formula. Further water content of the absorbent (1) was 0%.

Control 1

A similar procedure to Example 1 was repeated to obtain a control absorbent 1, except that the heat treatment was carried out for 10 minutes. The tests described in Example 1 were carried out by a similar method to Example 1 and the results are shown in Table 1.

EXAMPLE 2

A pulverized hydrated gel was obtained by the procedure of Example 1, except that 1.36 g of trimethylol propane triacrylate (0.020 mol % based on sodium acrylate possessing a neutralization ratio of 75 mol %) was used. The gel was dried by a similar method as in Example 1, to obtain a powder that passed through a 20-mesh metal gauze [absorbent resin powder (A-2)].

A liquid mixture containing, 1 part of glycerol, 3 parts of water and 8 parts of ethanol was mixed with 100 parts of the absorbent resin powder (A-2).

The resultant mixture was charged into a bowl dipped in an oil bath (195° C.) and was subjected to heat-treatment for 30 minutes under stirring to obtain an absorbent (2). The absorbent (2) thus obtained was subjected to the tests of Example 1 and the results are shown in Table 1.

EXAMPLES 3 and 4 and Control 2

A similar procedure to Example 2 was carried out to obtain absorbents (3) and (4) and control absorbent (2), except that the surface treatment liquids, composition, and heating conditions are as shown in Table 1. The performances of these samples are shown in Table 1.

EXAMPLE 5

100 parts by weight of the absorbent resin powder (A-2) and 1 part by weight of water-insoluble fine silica ("Aerosil 200" a trade name for a produce of Aerosil Co., Ltd.) was mixed by a V-type mixture to obtain absorbent resin powder B.

A liquid mixture containing 1 part of 1,3-propanediol, 15 parts of water and 15 parts of isopropanol was mixed with 101 parts of the absorbent resin powder B.

The resultant mixture was charged into a bowl dipped in an oil bath (210° C.) and was subjected to heat-treatment for 40 minutes under stirring to obtain an absorbent (5).

The absorbent (5) thus obtained was tested by a similar method to Example 1 and the results are shown in Table 1.

EXAMPLE 6

100 parts by weight of a commercially available starch-acrylic acid graft polymer (Sanwet IM-1000, manufactured by Sanyo Kasei Kogyo K.K.) and a liquid containing 1 part of glycerol and 8 parts of isopropanol were mixed. The resultant mixture was charged into a bowl dipped in an oil bath (210° C.) and was subjected to heat-treatment for 40 minutes under stirring to obtain an absorbent (6). The absorbent (6) thus obtained was tested by a similar method to Example 1, and the results are shown in Table 1.

TABLE 1

| | Absorbent Resin Powder A-1 | Example 1 | Control 1 | Absorbent Resin Powder A-2 | Example 2 | Example 3 | Example 4 |
|---|---|---|---|---|---|---|---|
| Precursor | | A-1 | A-1 | | A-2 | A-2 | A-2 |
| Absorption Capacity (g/g) | 54 | 54 | 54 | 62 | 62 | 62 | 62 |
| Precursor (parts) | | 100 | 100 | | 100 | 100 | 100 |
| Cross linking Agent | | Glycerol | Glycerol | | Glycerol | Glycerol | TMP |
| Cross linking Agent (parts) | | 0.75 | 0.75 | | 1 | 1 | 5 |
| Water (parts) | | 3 | 3 | | 3 | 4 | 5 |
| Hydrophilic Organic Solvent (parts) | | 12 | 12 | | 8 | 8 | 5 |
| Heater Conditions | | | | | | | |
| Temperature (°C.) | | 195 | 195 | | 195 | 195 | 210 |
| Time (min.) | | 45 | 10 | | 30 | 40 | 30 |
| Absorbent Properties | | | | | | | |
| Absorption Capacity (g/g) | 54 | 42 | 52 | 62 | 49 | 43 | 43 |
| Water-retaining property under pressure (ml/g) | | | | | | | |
| 10 min. | 8 | 21.5 | 11.5 | 7.5 | 22 | 24 | 23.5 |
| 30 min. | 10 | 25 | 15 | 9.5 | 27 | 29 | 23.5 |
| Liquid Permeability under pressure (sec) | 170 | 90 | 145 | 190 | 95 | 85 | 80 |
| Calculated Value of Formula | — | 77 | 95 | — | 78 | 69 | 71 |

| | Example 5 | Control 2 | Absorbent Resin Powder A-3 | Example 6 |
|---|---|---|---|---|
| Precursor | A-2 | A-2 | | A-3 |
| Absorption Capacity (g/g) | 62 | 62 | 65** | 65 |
| Precursor (parts) | 100 | 100 | | 100 |
| Cross linking Agent | 1,3-Propanediol | | | Glycerol |
| Cross linking Agent (parts) | 1 | 0 | | 1 |
| Water (parts) | 15 | 3 | | 0 |
| Hydrophilic Organic Solvent (parts) | 15 | 8 | | 8 |
| | Si 1 | | | |
| Heater Conditions | | | | |
| Temperature (°C.) | 210 | 195 | | 210 |
| Time (min.) | 40 | 30 | | 40 |
| Absorbent Properties | | | | |
| Absorption Capacity (g/g) | 36 | 62 | 65 | 48 |
| Water-retaining property under pressure (ml/g) | | | | |
| 10 min. | 23.5 | 7.5 | 7 | 15 |
| 30 min. | 25 | 9.5 | 10.5 | 18.5 |
| Liquid Permeability under pressure (sec) | 80 | 185 | 200 | 120 |

TABLE 1-continued

| | | | |
|---|---|---|---|
| Calculated Value of Formula | 58 | — | 71 |

*TMP: Trimethylolpropane
**water content 5%. Powder A-3

What is claimed is:

1. A method for treating the surface of an absorbent resin which comprises mixing (I) 100 parts by weight of an absorbent resin powder having a carboxyl group, (II) 0.01 to 30 parts by weight of a polyhydric alcohol, (III) 0 to 50 parts by weight of water and (IV) 0 to 60 parts by weight of hydrophilic organic solvent, and heat-treating at a temperature in the range of 90° to 250° C. to treat the surface of said absorbent resin powder (I) until the reaction of said absorbent resin powder (I) with said polyhydric alcohol (II) is completed, wherein the time for completion of the reaction is selected to satisfy the following equation (a-1):

$$30 \leq (100+C) B/A \leq 80 \qquad (a-1)$$

wherein A is the absorption capacity of said absorbent resin powder (I) for a physiological saline solution, B is the absorption capacity of the resultant treated absorbent resin for a physiological saline solution, and C is the parts by weight of said polyhydric alcohol (II) used per 100 parts by weight of said absorbent resin powder (I).

2. A method according to claim 1, wherein the amount of said polyhydric alcohol (II) is 0.1 to 10 parts by weight per 100 parts by weight of said absorbent resin powder (I).

3. A method according to claim 1, wherein the amount of water (III) is 0.01 to 20 parts by weight per 100 parts by weight of said absorbent resin powder (I).

4. A method according to claim 1, wherein the amount of said hydrophilic organic solvent (IV) is 0.1 to 20 parts by weight per 100 parts by weight of said absorbent resin powder (I).

5. A method according to claim 1, wherein the amount of water (III) is 0.1 to 20 parts by weight and the amount of said hydrophilic organic solvent (IV) is 0.1 to 20 parts by weight per 100 parts by weight of said absorbent resin powder (I).

6. A method according to claim 1, wherein the time for completion of the reaction is the time that satisfies the following equation (a-2):

$$40 \leq (100+C) B/A \leq 70 \qquad (a-2).$$

7. A method according to claim 1, wherein heat-treating is carried out in the presence of 0.01 to 10 parts by weight of a water-insoluble fine powder (V) until the reaction of said absorbent resin powder (I) with said polyhydric alcohol (II) is completed wherein the time for completion of the reaction is selected to satisfy the following equation (b-1):

$$30 \leq (100+C+D) B/A \leq 80 \qquad (b-1)$$

wherein A is the absorption capacity of said absorbent resin powder (I) for a physiological saline solution, B is the absorption capacity of the resultant treated absorbent resin for physiological saline solution, and C is parts by weight of said polyhydric alcohol (II) used per 100 parts by weight of said absorbent resin powder (I), and D is parts by weight of said water-insoluble fine powder (V) used per 100 parts by weight of the absorbent resin powder (I).

8. A method according to claim 7, wherein the amount of said water-insoluble fine powder (V) is 0.01 to 5 parts by weight per 100 parts by weight of the absorbent resin powder (I).

9. A method according to claim 7, wherein the particle size of said water-insoluble fine pwder (V) is less than about 50 μm.

10. A method according to claim 7, wherein said water-insoluble fine powder (V) is a water-insoluble inorganic fine powder.

11. A method according to claim 10, wherein said water-insoluble inorganic fine powder is at least one member selected from the group consisting of silicon dioxide, titanium dioxide, aluminum oxide, zeolite, kaolin, and hydrotalcite.

12. A method according to claim 7, wherein said water-insoluble fine powder (V) is mixed with said absorbent resin powder (I) before said absorbent resin powder (I) is mixed with said polyhydric alcohol (II), water (III) and hydrophilic organic solvent (IV).

13. A method according to claim 7, wherein said water-insoluble fine powder (V) is mixed with said absorbent resin powder (I) at a time when said absorbent resin powder (I) is mixed with said polyhydric alcohol (II), water (III) and hydrophilic organic solvent (IV).

14. A method according to claim 7, wherein the amount of said polyhydric alcohol (II) is 0.1 to 10 parts by weight per 100 parts by weight of said absorbent resin powder (I).

15. A method according to claim 7, wherein the amount of water (III) is 0.1 to 20 parts by weight per 100 parts by weight of said absorbent resin powder (I).

16. A method according to claim 7, wherein the amount of said hydrophilic organic solvent (IV) is 0.1 to 20 parts by weight per 100 parts by weight of said absorbent resin powder (I).

17. A method according to claim 7, wherein the amount of water (III) is 0.1 to 20 parts by weight and the amount of said hydrophilic organic solvent (IV) is 0.1 to 20 parts by weight per 100 parts by weight of said absorbent resin powder (I).

18. A method according to claim 7, wherein the time for completion of the reaction is the time that satisfies the following equation (b-2):

$$40 \leq (100+C+D) B/A \leq 70 \qquad (b-2).$$

19. The method for treating the surface of an absorbent resin of claim 1 wherein the heat-treatment is effected for at least about 30 minutes.

* * * * *